United States Patent

Klingler et al.

Patent Number: 5,679,873
Date of Patent: Oct. 21, 1997

[54] PROCESS FOR THE PRODUCTION OF DINITROTOLUENE

[75] Inventors: Uwe Klingler, Dormagen; Thomas Schieb, Rösrath; Gerhard Wiechers, Leverkusen, all of Germany; Jürgen Zimmermann, Walnut Creek, Calif.

[73] Assignee: Bayer Aktiengesellschaft, Leverkusen, Germany

[21] Appl. No.: 510,992

[22] Filed: Aug. 3, 1995

[30] Foreign Application Priority Data

Aug. 11, 1994 [DE] Germany .................. 44 28 459.4

[51] Int. Cl.⁶ .................................. C07C 205/06
[52] U.S. Cl. ............................. 568/934; 568/932
[58] Field of Search .................. 568/934, 932, 568/927

[56] References Cited

U.S. PATENT DOCUMENTS

| | | | |
|---|---|---|---|
| 3,928,475 | 12/1975 | Dassel | 260/645 |
| 4,021,498 | 5/1977 | Alexanderson et al. | 260/645 |
| 4,091,042 | 5/1978 | Alexanderson et al. | 260/645 |
| 4,453,027 | 6/1984 | Vaidyanathan | 568/937 |
| 4,496,782 | 1/1985 | Carr | 568/934 |
| 4,650,912 | 3/1987 | Pohl et al. | 568/924 |
| 4,663,490 | 5/1987 | Gerken et al. | 568/934 |
| 5,345,012 | 9/1994 | Schieb et al. | 568/934 |

FOREIGN PATENT DOCUMENTS

436 443   7/1991   European Pat. Off. .

OTHER PUBLICATIONS

Winnacker, Küchler, Chem Technol, vol. 2, Anorg. Technol. I. 4th Edition, 1982, pp. 70 to 72.
R.A. Vauck, H.A. Müller, Grundoperationen chemscher Verfahrensticknik, 5th Edition, VEB Leipzip, 1962 p. 447.

*Primary Examiner*—Marianne M. Cintins
*Assistant Examiner*—Dwayne C. Jones
*Attorney, Agent, or Firm*—Joseph C. Gil; Lyndanne M. Whalen

[57] ABSTRACT

Dinitrotoluene is produced in a two-stage process from toluene and nitric acid in the presence of sulfuric acid under adiabatic conditions in the presence of nitrating acids made up of specified components. The reaction product of the first phase is separated into an acid phase and an organic phase containing the mononitrotoluene. Some water is removed from the acid phase, nitric acid is added and the resultant mixture is recycled. The organic phase containing mononitrotoluene is further nitrated to produce the dinitrotoluene. This nitration mixture is also separated into an acid phase and an organic phase. The acid phase is treated to remove some water, nitric acid is added and the resultant acid mixture is recycled. Dinitrotoluene is recovered from the organic phase. This process is advantageous in that dilute nitric acid may be used and the heat of the nitration reaction is utilized.

10 Claims, No Drawings

PROCESS FOR THE PRODUCTION OF DINITROTOLUENE

BACKGROUND OF THE INVENTION

This invention relates to a two-stage process for the production of dinitrotoluene from toluene and nitric acid in the presence of sulfuric acid.

Dinitrotoluene (DNT) is used to produce tolylene diisocyanate (TDI). TDI is a starting material used in the production of polyurethane plastics. DNT is generally produced by reacting toluene with nitrating acid. This nitration reaction is carried out in two stages. Mononitrotoluene (MNT) is initially obtained by reacting toluene with a dilute nitrating acid. After removal of the spent sulfuric acid (hereinafter referred to as "waste acid"), the MNT is converted to DNT in a second process step. Both nitrating steps are carried out under isothermal conditions, i.e. with cooling to maintain a low temperature.

Two waste acids accumulate in the process and, after regeneration with nitric acid, may be returned to the process. The waste acid from the second stage can be directly recycled. The waste acid from the second stage may still have a concentration such that, after regeneration with nitric acid, it may be used without being concentrated beforehand. Accordingly, only the waste acid from the first stage has to be concentrated before being re-used. This is normally done by the Pauling process (Bedenbrenner, von Plessen, Vollmüller, *Dechema-Monogr.* 86 (1980), 197) although the vacuum process is also increasingly being used (Winnacker, Küchler, *Chem. Technol*, Vol. 2, *Anorg. Technol.* I, 4th Edition, 1982, pages 70 to 72). In both of these acid concentration processes, energy must be introduced to remove the water of reaction.

During its recycling, the concentrated waste acid is replenished with highly concentrated nitric acid. Although nitric acids of low concentration, which are far less expensive, could be used in principle, their use does involve the consumption of considerable additional energy because the waste acid has to be concentrated to a higher degree.

For the reasons mentioned above, efforts have long been made to improve the above-described nitration processes.

An improvement in terms of energy consumption may be achieved by carrying out the mononitration of benzene under adiabatic conditions. It was also found that it is possible to use more dilute nitric acids in such a process. The adiabatic process has been used industrially. See, for example, U.S. Pat. Nos. 3,928,475; 4,021,498; 4,091,042 and 4,453,027; and EP-A 436,443).

The adiabatic process was also applied to the production of aromatic dinitro compounds (EP-A 597,361). In this case, toluene is reacted with nitrating acid in a single stage to form DNT. By using nitrating acids with a special composition, it is possible to carry out the nitrating process under adiabatic conditions and to keep the heat of reaction in the system. There is no longer any need to cool the process, as in the conventional isothermal process, so that expensive cooling energy is saved. After separation of the phases, the hot waste acid is sprayed in vacuo and the heat of reaction of the process is used to concentrate the waste acid. Because the reaction is carried out under adiabatic conditions, i.e. at a high temperature, the process is able to accommodate the use of dilute nitric acid. Depending on the nitric acid used, there is little or no need for heating in the concentration step.

The disadvantage of this latter process is that both mononitration and dinitration are carried out with the same nitrating acid. Because nitration is intended to be quantitative, the reactivity of the nitrating acid has to be adapted to the dinitration step. Accordingly, the nitrating acid used in this known process is actually too concentrated for the mononitration step, so that mononitration takes place very quickly and, in some cases, with very little selectivity. Another disadvantage of this process is that a more concentrated waste acid than necessary accumulates in the mononitration step. Waste acids of relatively high concentration are much more expensive to concentrate in terms of energy because the heat of solution of water in sulfuric acid increases with increasing sulfuric acid concentration.

Another disadvantage of this known process is that DNT dissolved in the waste acid also distills over in the concentration step. Under the conditions required for condensation of the water, the DNT crystallizes, covers the heat exchanger and thus impedes the transfer of heat.

A possible solution to this problem with respect to heat transfer is to use cyclic heat exchangers. Cyclic heat exchangers are operated alternately and any coatings formed are melted off during the phase in which the heat exchanger is not in operation. Coatings formed on the heat exchange surfaces result in rapid reduction of cooling capacity. Consequently, the heat exchangers need to be frequently alternated. The removal of coatings formed from the inoperative condenser by melting requires additional energy.

Use of a mixing or injection condenser has been described as another possible solution to the problem of condensing solids-forming vapors (R. A. Vauck, H. A. Müller, *Grundoperationen chemischer Verfahrenstechnik*, 5th Edition, VEB Leipzig (1962), page 447). In the mixing or injection condenser, the vapors are introduced into a jet spray of cold water. DNT is deposited in the form of a fine particulate solid when such an injection condenser is used. In view of the large quantities of water required in these processes, the water is circulated and cooled in the return branch of the circuit. However, pipes and nozzles are subject to blockage by low melting, inorganic components which tend to become tacky.

One elegant solution to this problem is the isothermal two-stage nitration process. In this process, MNT from the first nitration stage is injected into the vapors of the second concentration stage. The MNT introduced reduces the melting point of the DNT isomer mixture and the condensed mixture remains liquid (DE-A 3,409,719).

SUMMARY OF THE INVENTION

It is an object of the present invention to provide a process for the production of dinitrotoluene in which dilute nitric acid may be used.

It is also an object of the present invention to provide a process for the production of dinitrotoluene which utilizes the heat of reaction.

It is a further object of the present invention to provide a process for the production of dinitrotoluene in which problems due to condensation of the vapors in the waste acid concentration step are avoided.

These and other objects which will be apparent to those skilled in the art are accomplished by nitrating toluene with a nitrating acid satisfying specified compositional criteria under adiabatic conditions to produce mononitrotoluene. The reaction mixture is then separated into an organic phase containing the mononitrotoluene and an acid phase. The mononitrotoluene is then further nitrated with a nitrating acid satisfying specified compositional requirements under adiabatic conditions to produce dinitrotoluene. The reaction mixture is then separated into an organic phase containing dinitrotoluene and an acid phase. The acid phase recovered after each separation may be further treated and recycled.

DETAILED DESCRIPTION OF THE INVENTION

The present invention relates to a two-stage process for the continuous production of dinitrotoluene isomer mixtures by nitration of toluene. In the first stage of this process, toluene and nitrating acid are reacted under adiabatic conditions in a continuously operated reactor at a temperature of from 0° to about 140° C., preferably from about 20° to about 140° C. The nitrating acid is made up of (i) from about 80 to about 100% by weight (based on total weight of nitrating acid used in the first stage) of inorganic materials which include: from about 60 to about 90% by weight (based on total weight of inorganic materials in nitrating acid used in the first stage) of sulfuric acid, from about 1 to about 20% by weight (based on total weight of inorganic materials in nitrating acid used in first stage) of nitric acid and at least 5% by weight (based on total weight of inorganic materials in nitrating acid used in first stage) of water; and (ii) from 0 to about 20% by weight (based on total weight of nitrating acid used in first stage) of organic materials which include from about 70 to about 100% by weight (based on total weight of organic materials in nitrating acid used in first stage) of nitrotoluene isomers with the remainder being by-products of the nitration reaction. The molar ratio of nitric acid to toluene is at least 0.7:1 and at most 1.2:1. The reaction mixture is then separated into an acid phase and an organic phase containing mononitrotoluene. At least 5% by weight of the water present in the acid phase is removed, preferably by distillation through flash evaporation. Nitric acid having a concentration of from 50 to 100% by weight is then added to the acid phase to replace the nitric acid consumed in the nitration reaction, if necessary, and is continuously returned to the reaction vessel in which the toluene and nitrating acid are reacted. The organic phase containing mononitrotoluene (MNT) removed in the first stage is then reacted under adiabatic conditions with a nitrating acid made up of (i) from about 80 to about 100% by weight (based on total weight of nitrating acid used in second stage) of inorganic materials which include from about 60 to about 90% by weight (based on total weight of inorganic materials in nitrating acid used in second stage) of sulfuric acid, from about 1 to about 20% by weight (based on total weight of inorganic materials in nitrating acid used in second stage) of nitric acid and at least 5% by weight (based on total weight of inorganic materials in nitrating acid used in second stage) of water; and (ii) from about 0 to about 20% by weight (based on total weight of nitrating acid used in second stage) of organic constituents which include from about 70 to about 100% by weight (based on total weight of organic materials in nitrating acid used in second stage) of nitrotoluene isomers with the remainder being by-products of the nitration reaction. This nitration reaction is carried out at temperatures of from about 20° to about 200° C., preferably at temperatures of from about 40° to about 180° C. and more preferably at temperatures of from about 60° to about 170° C. The MNT and nitrating acid are used in quantities such that the molar ratio of nitric acid to mononitrotoluene is at least 0.7:1 and at most 1.2:1. The reaction mixture is then separated into an acid phase and an organic phase containing dinitrotoluene. At least 5% by weight of the water present in the acid phase from the second stage of the nitration process is removed, preferably by distillation through flash evaporation, optionally with application of heat. Nitric acid having a concentration of from 50 to 100% by weight is then added to the acid phase before that acid phase is continuously returned to the reaction vessel. Mononitrotoluene from the first stage of the process is added to the vapors present during the concentration of the second waste acid.

The quantity of MNT added is selected so that the vapor condensate runs off in liquid form and does not form any solid coating. This may be achieved by, adding the MNT in an amount such that the ratio by weight of MNT to DNT present in the organic phase of the vapor condensate is from about 2:1 to about 10:1. After phase separation, the organic constituents of the vapor condensate are returned to the first and/or second nitration stage.

The process of the present invention is preferably carried out with two nitrating acids of different concentration. A nitrating acid of low concentration is preferably used in the first stage so that selective nitration and energy-optimized concentration of the waste acid are possible. A concentrated nitrating acid is used in the second stage in view of the greater nitrating demand.

Having thus described our invention, the following Examples are given as being illustrative thereof.

EXAMPLES

Example 1

The reactor used in each stage of the nitration process included a mixing nozzle (internal diameter 0.2 mm) and two redispersing nozzles (internal diameter 0.3 mm). Dwell zones (internal diameter 2.0 mm) optimized for the particular reaction were present between the individual nozzles.

100.5 g/h (1.090 moles/h) of toluene and 2,500 g/h (1.179 moles/h) of a nitrating acid composed of 72.4% by weight of sulfuric acid, 3.0% by weight of nitric acid and 24.6% by weight of water were continuously reacted under adiabatic conditions at 27° C. in a reactor such as that described above. The reaction mixture leaving the reactor was subjected to phase separation at approximately 50° C. The waste acid was passed through a concentration stage and, after replenishment with 60% nitric acid, was returned to the first reaction stage. The organic phase separated off was reacted under adiabatic conditions at a temperature of about 50° C. in a second reactor with 2038.8 g/h (1.168 moles/h) of a nitrating acid made up of 79.9% by weight of sulfuric acid, 3.6% by weight of nitric acid and 16.5% by weight of water. Phase separation was then carried out. After separation, the waste acid was passed through a concentration stage. To avoid deposits in the condensation section, 15 g/h of MNT from the first nitration stage were introduced into the superheated vapors of the evaporator. After replenishment with 60% nitric acid, the concentrated waste acid was returned to the second nitration stage, as were the organic constituents of the vapor condensate. The organic phase was washed in the usual way (with water and soda) and yielded 196.8 g/h of dinitrotoluene (99.0%).

Example 2

101.2 g/h (1.102 moles/h) of toluene and 2,500 ml/h (1.1903 moles/h) of a nitrating acid composed of 68.5% by weight of sulfuric acid, 3.0% by weight of nitric acid, and 28.5% by weight of water were continuously reacted under adiabatic conditions at 85° C. in a reactor such as that described in Example 1. The reaction product leaving the reactor was separated into two phases at approximately 50° C. The waste acid was delivered to a concentration stage and, after replenishment with 60% nitric acid, was returned to the first reaction stage. The organic phase containing mononitrotoluene was then reacted under adiabatic conditions with 2,072.9 g/h (1.183 moles/h) of a nitrating acid made up of 77.9% by weight of sulfuric acid, 3.6% by weight of nitric acid and 18.5% by weight of water in a second reactor. The temperature at which this reaction began corresponded to the temperature of the recycled concentrated waste acid from the same stage after concentration and replenishment with fresh nitric acid. The dinitrotoluene was then isolated by phase separation and washed in the usual way with water and soda. The waste acid obtained was concentrated. To avoid deposits in the condensation section, 8 g/h of MNT from the first nitration stage were introduced into the superheated vapors of the evaporator. After replenishment with 60% nitric acid, the concentrated waste acid was returned to the second nitration stage, as were the organic constituents of the vapor condensate. In continuous operation with closed circuits, the yield of dinitrotoluene was 197.6 g/h (98.7%).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A continuous process for the production of dinitrotoluene isomer mixtures comprising
    (A) reacting
        (1) toluene with
        (2) nitrating acid which is made up of
            (i) from about 80 to about 100% by weight of inorganic materials which include:
                (a) from about 60 to about 90% by weight of sulfuric acid,
                (b) from about 1 to about 20% by weight of nitric acid and
                (c) at least 5% by weight of water
            and
            (ii) from 0 to about 20% by weight of organic materials of which at least 70% by weight are isomers of nitrotoluene
    in amounts such that the molar ratio of nitric acid to toluene is between 0.7:1 and 1.2:1 under adiabatic conditions in a continuously operated reactor at a temperature of from about 0° to about 140° C.,
    (B) separating the reaction mixture of (A) into an acid phase and an organic phase containing mononitrotoluene,
    (C) removing at least 5% by weight of water from the acid phase separated in (B),
    (D) adding nitric acid to the acid phase from (C),
    (E) recycling the acid phase from (D),
    (F) reacting the mononitrotoluene in the organic phase from (B) with a nitrating acid which is made up of
        (i) from about 80 to about 100% by weight of inorganic materials which include:
            (a) from about 60 to about 90% by weight of sulfuric acid,
            (b) from about 1 to about 20% by weight of nitric acid and
            (c) at least 5% by weight of water
        and
        (ii) from 0 to about 20% by weight of organic materials of which 70% by weight or more are isomers of nitrotoluene
    in amounts such that the molar ratio of nitric acid to mononitrotoluene is between 0.7:1 and 1.2:1 under adiabatic conditions at a temperature of from about 40° to about 180° C. and
    (G) separating the reaction mixture of (F) into an acid phase and an organic phase containing dinitrotoluene,
    (H) removing at least 5% by weight of water from the acid phase from (G),
    (I) adding mononitrotoluene to the vapors generated in (H),
    (J) adding nitric acid to the acid phase from (H),
    (K) recycling the acid phase from (J) to the reaction vessel in which (F) is carried out,
    and
    (L) recovering dinitrotoluene from the organic phase of (G).

2. The process of claim 1 in which nitric acid having a concentration of from 50 to 100% by weight is added in (D).

3. The process of claim 2 in which the water is removed from the acid phase by flash evaporation.

4. The process of claim 2 in which nitric acid having a concentration of from 50 to 100% by weight is added in (J).

5. The process of claim 4 in which the water is removed from the acid phase by flash evaporation.

6. The process of claim 1 in which nitric acid having a concentration of from 50 to 100% by weight is added in (J).

7. The process of claim 6 in which the water is removed from the acid phase by flash evaporation.

8. The process of claim 1 in which (A) is carried out at a temperature of from about 20° to about 140° C.

9. The process of claim 1 in which (F) is carried out at a temperature of from about 40° to about 180° C.

10. The process of claim 1 in which (F) is carded out at a temperature of from about 60° to about 170° C.

* * * * *